United States Patent [19]

Smith, Jr.

[11] Patent Number: 5,342,753
[45] Date of Patent: Aug. 30, 1994

[54] BLOOD COLLECTING TUBE WITH BLOOD FACTOR ANTIBODIES AS ANTICOAGULANT

[76] Inventor: William I. Smith, Jr., 1061 Lindendale Dr., Mt. Lebanon, Pa. 15243

[21] Appl. No.: 814,726

[22] Filed: Dec. 26, 1991

Related U.S. Application Data

[63] Continuation-in-part of Ser. No. 366,735, Jun. 15, 1989, abandoned.

[51] Int. Cl.$^5$ .................. A01N 1/02; A61K 39/00; A61K 37/04; A61B 5/14
[52] U.S. Cl. ........................ 435/2; 530/381; 530/383; 530/384; 530/388.25; 530/389.3; 128/764
[58] Field of Search ................ 435/2, 7, 4, 13, 973; 530/381, 383, 384; 128/764; 424/85.8

[56] References Cited

U.S. PATENT DOCUMENTS

| | | | |
|---|---|---|---|
| 3,890,955 | 6/1975 | Elliott | 128/2 F |
| 3,901,219 | 8/1975 | Kay | 128/764 |
| 4,061,466 | 12/1977 | Sjoholm et al. | 23/230 B |
| 4,085,737 | 4/1978 | Bordow | 128/2 F |
| 4,308,232 | 12/1981 | Crouther et al. | 422/102 |
| 4,361,509 | 11/1982 | Zimmerman et al. | 260/112 B |
| 4,553,553 | 11/1985 | Homann et al. | 128/749 |
| 4,592,994 | 6/1986 | Mattiasson | 435/7 |
| 4,666,850 | 5/1987 | Mehl et al. | 435/243 |
| 4,668,621 | 5/1987 | Doellgast | 435/13 |
| 4,675,159 | 6/1987 | Al-Sioufi | 128/764 |
| 4,677,055 | 6/1987 | Dodin et al. | 435/7 |
| 4,831,119 | 5/1989 | Nordfang et al. | 530/383 |
| 4,936,314 | 6/1990 | Kasai et al. | 128/764 |
| 4,970,300 | 11/1990 | Fulton et al. | 530/383 |

FOREIGN PATENT DOCUMENTS

| | | |
|---|---|---|
| 0116793 | 8/1984 | France . |
| 56-115725 | 9/1981 | Japan . |
| 63-22030 | 1/1988 | Japan . |
| 8204264 | 12/1982 | PCT Int'l Appl. . |

OTHER PUBLICATIONS

Todd–Sanford, *Clinical Diagnosis By Laboratory Methods*, 1974, p. 103 (Davidsohn et al.).

Andes, W. A., "IgM anticoagulant with acquired abnormalities in factor VIII", *Thromb Res*, Sep. 15, 1982, 27 (6), pp. 703–712.

Tsao et al., "The Removal of Adventitious Viruses and Virus–Infected Cells Using a Cellular Adsorbent: A Feasibility Study", *Bio/Technology*, Nov. 1988 pp. 1330–1333.

*Primary Examiner*—Douglas W. Robinson
*Assistant Examiner*—John P. Weber
*Attorney, Agent, or Firm*—Arnold B. Silverman; David V. Radack

[57] ABSTRACT

An apparatus for resisting coagulation of blood, includes a blood container having disposed therein antibody to blood coagulation factors for resisting coagulation of blood. The apparatus further includes a needle and a holder for the needle which are both operatively associated with the blood container. The blood coagulation factor antibody inhibits coagulation of the blood drawn by the needle into the blood container so that an uncoagulated blood sample is obtained.

1 Claim, 2 Drawing Sheets

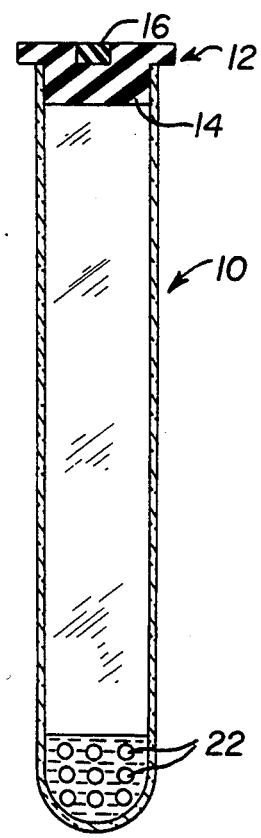
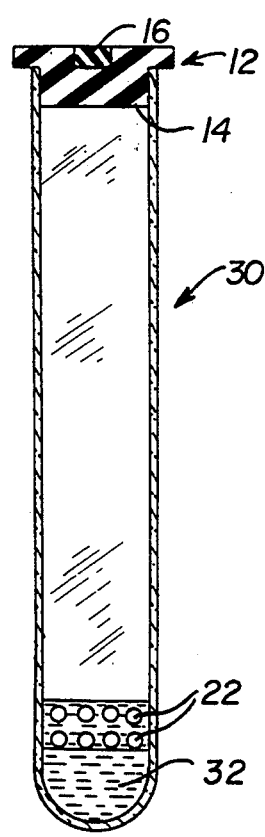
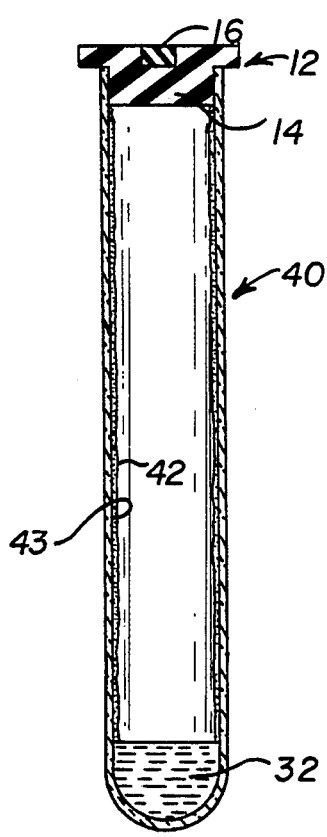
FIG. 1          FIG. 2          FIG. 3
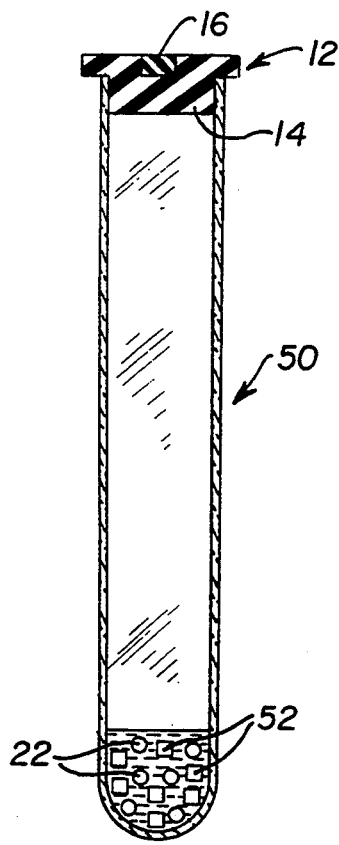
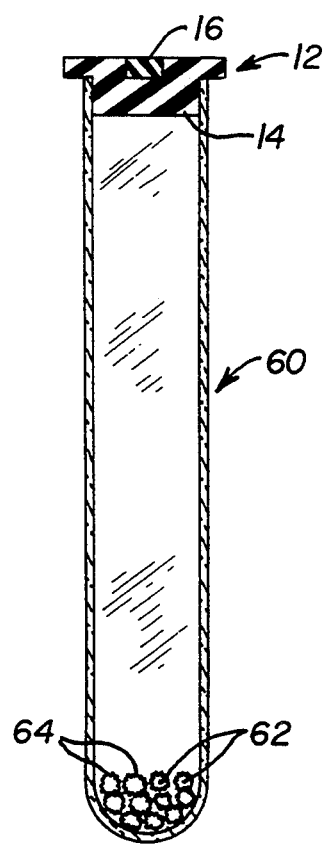
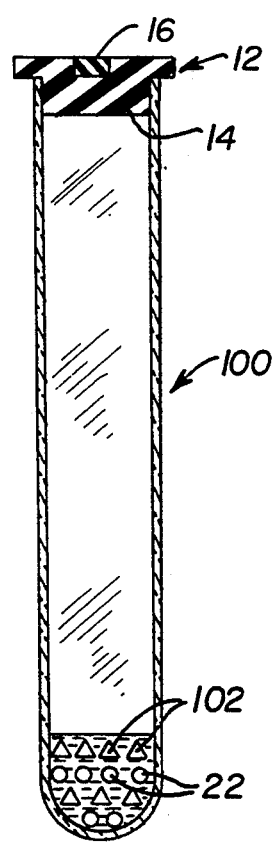
FIG. 4          FIG. 5          FIG. 6

BLOOD COLLECTING TUBE WITH BLOOD FACTOR ANTIBODIES AS ANTICOAGULANT

CROSS-REFERENCE TO RELATED APPLICATION

This application is a continuation-in-part of U.S. patent application Ser. No. 07/366,735 filed Jun. 15, 1989, now abandoned.

BACKGROUND OF THE INVENTION

1. Field Of The Invention

This invention relates to a method and apparatus for inactivating infectious agents in and resisting coagulation of biological fluids, and more particularly to providing antibodies in evacuated tubes before the biological fluid is introduced into the tube.

2. Description Of The Prior Art

In the evaluation and care of patients, it is often necessary to obtain blood samples. The routine procedure for drawing blood from a patient requires a needle holder, a disposable needle, and multiple evacuated tubes. A disposable needle is attached to the holder, the needle is inserted into the patient's vein and the evacuated tube is inserted through the opposite end of the needle into the holder. The evacuated tube is then allowed to receive the derived quantity of blood. The tube is then removed and another may be employed, if desired.

During the above process, the health care worker may be exposed to blood which drips from the end of the needle or may be injured by sticking the needle into his or her skin. In addition, the cap may accidentally come off of the tube or the tube may break, splashing the health care worker with blood. Laboratory workers, also, are exposed to the blood in the process of handling the blood filled tube and in disposing of the needle.

If a patient's blood contains infectious agents, health care workers may be exposed to these infectious agents and thus are at risk of acquiring infection. The Center For Disease Control has estimated that 500 to 600 health care workers are hospitalized annually due to occupationally acquired Hepatitis B Virus ("HBV"). *U.S. Dept. of Labor and U.S. Dept. of Health and Human Services, Joint Advisory Notice on Protection Against Occupational Exposure to HBV and HIV,* pages 1-13 Oct. 30, 1987. Of these, over 200 deaths resulted. Other infectious agents, such as Human Immunodeficiency Virus ("HIV"), Human T Lymphotropic Virus I ("HTLV I"), and Cytomegalovirus ("CMV") cause infections less often, but still pose a significant threat to the health care worker.

It is known to provide a blood collection tube and method that attempts to disinfect infectious viral contaminants instantaneously when the blood is taken. U.S. Pat. No. 4,675,159 discloses using a disinfectant material, such as aldehyde (with gluteraldehyde being preferred), in connection with a blood collection tube. The amount of aldehyde based disinfectant positioned in the container is adjusted to provide an ultimate concentration of aldehyde in the blood specimen of about 0.1 to 2.5 percent by weight and is buffered to a pH of about 7.2 to 8.5 percent. The aldehyde based substances disinfect blood by cross-linking and/or polymerizing amino groups on the surface of the infectious agent.

The problem with using aldehyde based substances is that the above-described polymerization distorts and destroys the structure and function of proteins. When used in biologic situations, a gluteraldehyde, for example, does not distinguish between the amino groups of infectious agents and the amino groups of the patient's blood and serum proteins. Ultimately, this cross-linking leads to coagulation which renders the blood sample unsuitable for routine processing. Also, the patient's altered proteins are unsuitable for analysis. Lowering of gluteraldehyde concentrations is not a solution because of the loss of ability to inactivate the infectious agents.

Other disadvantages of aldehyde based disinfectants are that they are unstable and that they cannot be used with heparin.

U.S. Pat. No. 4,308,232 discloses an anticoagulant stopper coating which resists adherence of cells to the stopper. The coating consists of a blood anticoagulant, a binding agent layer, and an outer layer of silicone oil.

U.S. Pat. No. 3,890,955 discloses a vacuum indicator. A standard blood collection tube having a partial vacuum pressure and a needle for removing blood from a patient is provided. A material, which is coated on the tube, changes color to indicate when vacuum pressure is lost in the tube.

U.S. Pat. No. 3,901,219 discloses a blood collecting container and method consisting of a tube having a stopper and a piston barrier which holds a chemical which can be added to the collected blood. When blood is introduced into the tube, the piston barrier descends (FIG. 2) until reaching constriction. FIG. 3 illustrates the apparatus with collected blood after it has been centrifuged.

Despite these known apparatus and methods there still remains a need for an effective way to prevent accidental infection of health care workers.

It is also desired, in evaluating blood constituents such as blood gases and potassium, to obtain an anticoagulated specimen. It is known to add EDTA (or equivalent chemical agents such as oxylate and citrate) or heparin to the drawn blood to obtain an anticoagulated specimen. The EDTA chelates calcium ions. These calcium ions are necessary for the functioning of many of the blood clotting factors (factors II, V, VII, VIII, IX and X). By removing the calcium, the effective functioning of the blood clotting factors is inhibited and the blood does not clot. Heparin functions through interaction with Antithrombin III and binding to factors XII, XI, IX, X and II. The binding inhibits the functioning of the factors and resists coagulation.

The problem with using chelating agents such as EDTA is that these cause water to leave cells and enter the plasma which causes mild dilution of the plasma. In addition, chelating agents cannot be used for blood gas determinations and when ions, such as calcium, are desired to be measured.

Heparin, which is a heterogenous mixture of linear and ionic polyelectrolytes, is not uniform in its effects. Heparin preparations have ranging solubilities and anticoagulative properties, and so must be used in excess to achieve reproducible coagulation. Heparin also precipitates fibronectin, a blood protein, which clogs the small orifices of blood gas instruments. Heparin binds calcium and therefore is not suitable for ionized calcium determinations. Likewise, heparin may bind certain antibiotics such as aminoglycosides.

Thus, there remains a need for a method and apparatus for inactivating infectious agents in and resisting coagulation of biological fluids. This method should not only effectively disinfect infectious agents, but also not adversely affect the other constituents of the particular biological fluid to be analyzed. There also remains a need for a method of resisting coagulation of biological fluids that can allow effective analysis of certain blood constituents such as blood gases and potassium.

SUMMARY OF THE INVENTION

The herein disclosed invention meets these needs. The method and apparatus for inactivating infectious agents in biological fluid samples involves providing a biological fluid tube having disposed therein a volume of antibodies. These antibodies react rapidly with the biological fluid to inactivate the infectious agents therein as the biological fluid enters the tube. The antibody can be secured to the sides of the tube or can be contained on glass or nylon beads disposed in the tube, for example. After the biological fluid is introduced in the tube, the infectious agents will bind to the antibodies, thus reducing the chance the health care worker will be exposed to the infectious agent.

The method and apparatus for resisting coagulation in a biological fluid involves adding an antibody or antibodies to a blood sample. These antibody or antibodies have an anticoagulative effect on the blood and thus would allow evaluation of certain blood constituents such as blood gases and potassium.

It is an object of the invention to provide a biological fluid collection tube having disposed therein antibody or antibodies for the deactivation of infectious agents in patient drawn biological fluid.

It is a further object of the invention to provide a method and apparatus which will quickly and efficiently inactivate infectious agents while not having a significant effect on other blood constituents.

It is a further object of the invention to provide several methods of providing the antibody or antibodies in the collection tube.

It is a further object of the invention to provide a disinfectant method that may be used with a wide variety of anticoagulants and with silicone gel.

It is a further object of the invention to provide that both polyclonal and monoclonal antibodies can be used as the disinfectant agent.

It is a further object of the invention to provide a method of disinfecting blood in a tube which requires only minimal volumes of disinfectant to be used.

It is a further object of the invention to provide a method of resisting coagulation in a biological fluid by adding thereto a quantity of antibodies.

It is a further object of the invention to provide an anticoagulative that does not interfere with the testing of the biological fluid.

It is a further object of the invention to provide an antibody anticoagulative that has minimal chelating properties, negligible water shift, and low ionic concentration.

It is a further object of the invention to provide an antibody anticoagulative that is uniform and that does not react with fibronectin and calcium.

It is a further object of the invention to provide an antibody anticoagulative that can assay blood gases, ionized calcium, potassium, aminoglycosides, antibiotics and cell numbers.

It is a further object of the invention to provide an antibody anticoagulative that is easy to prepare, inexpensive and that does not pose a chemical or biologic hazard to health care workers.

These and other objects will become apparent from the description of the invention with reference to the drawings appended to this application.

BRIEF DESCRIPTION OF THE DRAWINGS

FIG. 1 shows a blood collection tube having an amount of an antibody disposed therein.

FIG. 2 shows a blood collection tube having an amount of an antibody and an amount of silicone gel disposed therein.

FIG. 3 shows a blood collection tube in which the antibodies are dried and coated on the inside surface of the blood collection tube.

FIG. 4 shows a blood collection tube in which the antibody and an anticoagulant are disposed.

FIG. 5 shows a blood collection tube having a plurality of glass beads on each of whose surfaces is disposed an amount of an antibody.

FIG. 6 shows a blood collection tube having contained therein an amount of anticoagulative antibody/antibodies.

DESCRIPTION OF THE PREFERRED EMBODIMENT

Figure 7:
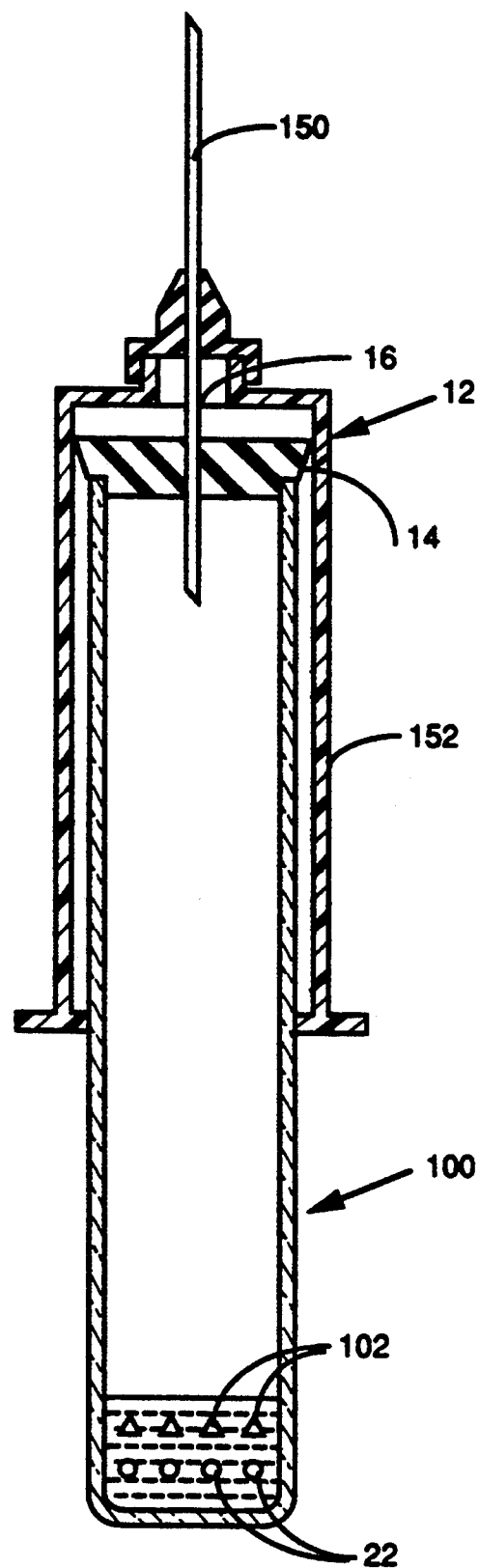
FIG. 7 is a vertical sectional view showing the blood collection tube, the holder means and the needle of the invention.

As used herein, "patient" means members of the animal kingdom including humans, regardless of whether the person or animal is ill.

Referring to FIG. 1, there is shown a standard blood collection tube 10 that is used in connection with drawing blood from a patient. This tube is equipped with a stopper 12 which consists of a body portion 14 made of rubber and a needle entry portion 16. The blood collection tube 10 may, for example, hold about 10.00 ml of fluid. As is well known, this blood collection tube 10 is used with a needle holder and a disposable needle (both not shown). The disposable needle is attached to the holder, the needle is inserted into the patient's vein and the needle entry portion of the stopper 12 is inserted through the opposite end of the needle into the holder. The blood collection tube 10 is then allowed to receive blood and when the desired amount of blood has been collected the blood collection tube is removed and another may be used. In this fashion, multiple tubes of blood may be obtained from a single needle stick.

The blood collection tube 10 of FIG. 1 contains a desired amount of antibody 22. The antibody is preferably in a liquid form, such as an electrolyte solution composed predominantly of NaCl in physiologic concentrations. Because of the high specificity and collection of antibodies, in general, only minimal volumes of antibody will be needed. The volume of antibody 22 disposed in the tube 10 is about 0.01 ml to 1.00 ml of antibody, with 0.10 ml to 0.20 ml being preferred. This will provide a dilutional effect of approximately 0.01 to 2.0 ml, with 0.10 to 0.20 ml being preferred. The antibody will be about 0.10% to 20% of the volume of the blood with about 0.50% to 1.00% being preferred.

The antibody can either be a polyclonal or a monoclonal antibody, used either alone or in combination.

Upon the introduction of blood, the swirling action of the blood entering the evacuated tube will mix the antibodies and blood. Further mixing may be achieved by inverting the tube, as is commonly done following the collection of blood. Antibodies have high affinity constants, in the range of $10^{-9}$ to $10^{-12}$ L/M, and react rapidly and completely with their preferred antigen (e.g., infectious agents or coagulation proteins) to form a complex, as is illustrated by the following:

Antibody(Ab) + Infectious Agent(IA) ⟶

Antibody-Infectious Agent Complex(IA − Ib)

Following formation of the complex, certain blood proteins called complement proteins bind to the antigen-antibody complex. The binding of complement may lead to the direct inactivation of infectious agents or to the phagocytosis of the complex and agent by the white blood cells present in blood.

Ab − IA + Complement(C) ⟶

Ab − IA − C(destruction or inactivation of infectious agent)

Ab − IA − C + white blood cells ⟶ phagocytosis(inactivation of infectious agent)

These reactions take place quickly and are completed in seconds to minutes. The binding of antibodies to infectious agents in a liquid phase is fast and complete, usually occurring in less than 1 second. Solid phase reactions (reactions when the antibody is bound to beads or coated to the tube) take longer, on the order of several minutes.

These antibodies have been demonstrated to be effective in inactivating HIV and HBV. Centers for Disease Control: *Recommendations For Prevention Of HIV Transmission In Health Care Settings.* Morbidity and Mortality Weekly Report Supplement, 36 (25) 15–165, Aug. 21, 1987.

Referring now to FIG. 2, a blood collection tube 30, having a similar stopper 12 as was described in FIG. 1, is shown having an amount of antibody 22 and a silicone gel 32. The amount of silicone gel used is about 0.50 ml to 2.00 ml with about 0.50 ml to 1.00 ml being preferred. As the silicone gel 32 is inert, it does not dilute the blood collected in tube 30. As is known to those skilled in the art, the silicon gel 32 is used to facilitate the separation of the serum from the cellular elements of a patient's blood. Silicon gel 32 is preferred for those assays requiring serum. The cellular constituents will be separated from the serum and intracellular viruses will therefore no longer be available for infecting the laboratory worker.

FIG. 3 shows a blood collection tube 40 having a similar stopper 12 as was described hereinabove, in which the antibody 42 is dried and coated on the inner surface 43 of the tube 40. This is done by introducing into the tube 40 a volume of antibody sufficient to inactivate the infectious agents and then drying this volume of antibody to the tube's 40 surface. The coating thickness of the antibody is less than 1.00 mm. The antibody preferably covers about 5% to 75% of the inside surface of the tube 40. It is preferred to provide the silicone gel 32 in this embodiment. The coating 42 is preferably not dried on to the inner surface 43 occupied by the silicone gel 32. The antibody can bind to an infectious agent in the blood sample and both can thus be removed from a biological fluid solution as was explained hereinabove.

FIG. 4 shows a blood collection tube 50 and stopper 12 having an antibody 22 along with an anticoagulant 52. The anticoagulant 52 (indicated by squares) can be selected from the group consisting of heparin, EDTA and citrate. The amount of anticoagulant 52 is about 0.10 to 2.00 ml, with about 0.50 to 1.00 ml being preferred, or about 10% to 20% by volume to the amount of blood collected in the tube 50.

FIG. 5 shows another embodiment of the invention. The blood collection tube 60 (with stopper 12) has disposed therein a plurality of glass beads 62. These beads can be made of nylon, glass, latex, resin or other inert materials. The antibody 64 is adhered to the outside surface of the glass beads 62. The infectious agents in the blood will bind to the antibody and thus will be removed from the biological fluid.

It will be appreciated that only certain examples of combinations of antibody, anticoagulant, and silicone gel were discussed hereinbefore. The invention, however, is not limited to these combinations.

It will be appreciated that the invention cannot be used to analyze the presence of antibody-specific virus or antibody to a specific virus. That is, if antibody HBV and HIV is added to a tube, the blood sample obtained in that tube cannot be used to evaluate the patient's antibodies to HIV and HBV or analyzed for the presence of HIV or Hepatitis B Surface Antigen.

The invention provides a blood collection tube and associated method that not only inactivates viruses and other infectious agents present in a patient's blood, but also does not have a measurable effect on other constituents of the blood, therefore, allowing the blood to be used for the analyses for which the blood was drawn.

As was mentioned hereinabove, it is sometimes desirable to obtain an anticoagulated blood sample. The clotting of blood involves the sequential interactions of a series of plasma proteins in a highly ordered and complex fashion, as well as interaction of these complexes both with blood plasma and with materials released from tissues. Blood factor anticoagulant antibodies essentially block pathways in this complex series to resist coagulation of the blood. The method of the invention provides for using antibodies to inhibit clotting factors in the blood and to resist coagulation in blood samples obtained for laboratory analysis at the point where the blood is drawn from the patient.

FIG. 6 shows a biological fluid containing tube 100 (with stopper 12) in which is contained an amount of antibody 22 and a blood coagulation factor antibody 102 (indicated by triangles). The volume of blood coagulation factor antibody 102 disposed in the tube will be about 0.10 to 20% of the volume of the blood with about 0.50 to 1.00% being preferred. Referring to FIG. 7 the biological fluid containing tube 100 is used in operative association with a needle 150 and holder means 152. Blood is drawn from the patient through the needle and is collected in the biological fluid containing tube 100 containing the blood factor antibody 102.

The antibody 102 binds to one or several of the blood coagulation factors including factors I (fibrinogen), II (prothrombin), V, VII, VIII, IX, X, XI, XII and resists coagulation of the blood. The antibodies 102 differ in specificity (the compound to which the antibody binds) from anti-infectious agent antibodies. Coagulation factor antibodies bind to the specific active portions of coagulation proteins, thereby inhibiting their biologic function. The binding of the antibody to the specific coagulation protein inhibits the coagulation process.

The uncoagulated blood may then be assayed, the formed elements (red blood cells white blood cells) may be separated and the plasma used for analysis, and the cellular elements may be isolated and analyzed.

The blood coagulation factor antibody consists of solutions of one or more of the following blood coagulation factor antibodies: I, II, V, VII, VIII, IX, X, XI and XII. It is preferred to use a solution consisting of a blood coagulation factor antibody to the intrinsic pathway and a blood coagulation factor antibody to the common pathway. Blood coagulation factor antibodies to the intrinsic pathway are antibodies to factors VIII and IX, for example, and blood coagulation factor antibodies to the common pathway are antibodies to factors I, II, V and X, for example.

The coagulant antibodies can be produced in goats, rabbits and horses or may be monoclonal antibodies which are produced through immunization of rats or mice. Purified anticoagulant antibodies are also commercially available. These antibodies are easy to produce, inexpensive and do not pose a chemical or biologic hazard to health care workers.

Antibody anticoagulation has the benefits of heparin (minimal chelating properties, negligible water shift and low ionic concentration) and lacks heparin's disadvantages (uniform preparation, noninteraction with fibronectin and calcium). Antibody anticoagulated blood may be used to assay blood gases, ionized calcium, potassium, aminoglycoside antibiotics, and cell numbers.

EXPERIMENTAL RESULTS

The following antibodies to blood coagulation factors were obtained from commercial sources:

| | |
|---|---|
| Anti-Factor VIII | (intrinsic pathway) |
| Anti-Factor IX | (intrinsic pathway) |
| Anti-Factor X | (common pathway) |
| Anti-Factor V | (common pathway) |
| Anti-Factor II | (common pathway) |
| Anti-Factor I | (common pathway) |

100 microliters of each of the six anti-factor antibodies were drawn into six separate syringes. After this, 1 ml of whole blood was drawn into each of the six syringes. In addition 1 ml of whole blood was drawn into a control syringe containing no anti-factor antibody. The separate syringes were emptying into test tubes for evaluation of clotting. Table I lists the anti-factor antibody (and control syringe) and their respective clotting times (rounded to the nearest minute). The tests were done at room temperature. Clotting times were determined by tilting the tube and determining whether or not the specimen is a liquid or turned to a gel (clot).

TABLE 1

| Anti-Factor Antibody | Clotting Time (Minutes) |
|---|---|
| Control | 5 Minutes |
| VIII | 10 Minutes |
| V | 21 Minutes |
| IX | 32 Minutes |
| I | 5 Minutes |
| II | 11 Minutes |
| X | >180 Minutes |

It can be seen that all of the anti-factor antibodies inhibited coagulation, however only anti-factor antibody X was moderately effective (no clotting after 180 minutes of observation). However, this blood sample formed a clot after being at 4° C. overnight.

Additional tests were performed employing combinations of the anti-factor antibodies in mixtures. The combinations were mixtures of 50 microliters of each of the anti-factor antibodies into separate syringes. Thus, for combinations of two antibodies, the syringe contains 100 microliters, comprised of 50 microliters of one antibody and 50 microliters of another antibody. For combinations of three antibodies, the syringe contained 150 microliters; 50 microliters of the first antibody; 50 microliters of the second antibody and 50 microliters of the third antibody. In all, eight combinations were created in eight separate syringes. Again, 1 ml of blood was introduced into each of the eight syringes. The blood and antibody combinations were emptying into separate test tubes. The resulting clotting times are reported in Table II (rounded to the nearest minute).

TABLE II

| Anti-Factor Antibody | Clotting Time (Minutes) |
|---|---|
| VIII + II | 7 Minutes |
| VIII + II | 8 Minutes |
| VIII + V | 11 Minutes |
| VIII + X | 25 Minutes |
| VIII + IX + V | 22 Minutes |
| VIII + IX + II | 24 Minutes |
| VIII + IX + I | 32 Minutes |
| VIII + X + IX | >180 Minutes |

It can be seen again, that all of the anti-factor antibodies inhibited coagulation. The preferred combination is VIII+X+IX in that the blood was still liquid after 14 hours after the start of the experiment.

In order to test whether the anti-factor antibody combination of VIII+X+IX affected certain blood properties, the blood sample plus antibody combination was measured for T4 (thyroxine) and TSH. A radioimmuno assay was used to measure T4. An immunoradiometric assay was used to measure TSH. T4 is a hormone present in low levels of blood and is measured as micrograms per 100 ml. TSH is a polypeptide hormone and sensitive to degradation and is measured as micro International units per ml. These are very sensitive laboratory tests which allow assessment of the effects of the antibodies on the blood. Four samples of the anticoagulated blood were tested for T4 and four samples of the anticoagulated blood were tested for TSH. These were compared to the control blood which did not contain any anti-factor antibody. Table III lists the results of these tests.

TABLE III

| | | Antibody Anticoagulated Samples | Control Samples | % Recovery |
|---|---|---|---|---|
| T4: | Sample 1 | 5.7 | 6.4 | 89 |
| | Sample 2 | 6.1 | 6.5 | 95 |
| | Sample 3 | 5.9 | 6.4 | 92 |
| | Sample 4 | 6.4 | 6.3 | 100 |
| TSH: | Sample 1 | 3.3 | 3.2 | 100 |
| | Sample 2 | 3.1 | 3.3 | 95 |
| | Sample 3 | 3.2 | 3.3 | 100 |
| | Sample 4 | 3.3 | 3.2 | 102 |

The recoveries of T4 and TSH ranged from 89% to 102%, with an average of 100% for TSH and 94% for T4. These recoveries are within expected experimental errors for these assays. This means that there is no statistically significant difference in the measurements of the amounts of T4 and TSH in the antibody anticoagulated sample and control serum.

It will be appreciated that a method and apparatus for inactivating infectious agents in and resisting coagulation of biological fluids is provided. The method and apparatus utilize antibodies which are relatively inexpensively commercially available and which present no biologic or health hazard to the medical worker.

Whereas particular embodiments of the invention have been described above for purposes of illustration, it will be appreciated by those skilled in the art that numerous variations of the details may be made without departing from the invention as described in the appended claims.

I claim:

1. An apparatus for containing blood from a patient comprising:

a blood container means having disposed therein antibody to blood coagulation factors for resisting coagulation of said blood;

a needle;

holder means to hold said needle, said holder means being operatively associated with said blood container means, whereby said needle draws said blood from said patient and deposits the same into said blood container means such that blood coagulant factors in said blood will be inhibited so that said blood sample will be uncoagulated;

said blood coagulation factor antibody is a combination of blood factor antibody to the intrinsic pathway and a blood factor antibody to the common pathway; and said combination is antibody to blood Factor VIII; antibody to blood Factor IX; and antibody to blood Factor X.

* * * * *